United States Patent [19]

Bornzin et al.

[11] Patent Number: 5,628,779
[45] Date of Patent: May 13, 1997

[54] SINGLE-PASS A-V PACING LEAD

[75] Inventors: Gene A. Bornzin; Kevin L. Morgan, both of Simi Valley; Joseph J. Florio, Sunland; Wendy K. Wolsleger, Cherry Valley, all of Calif.

[73] Assignee: Pacesetter, Inc., Sylmar, Calif.

[21] Appl. No.: 629,960

[22] Filed: Apr. 3, 1996

[51] Int. Cl.⁶ ........................................... A61N 1/05
[52] U.S. Cl. ............................................. 607/123; 607/125
[58] Field of Search ......................... 607/116, 119, 607/122, 123, 125, 126; 128/642

[56] References Cited

U.S. PATENT DOCUMENTS

| | | |
|---|---|---|
| 4,154,247 | 5/1979 | O'Neill . |
| 4,393,883 | 7/1983 | Smyth et al. . |
| 4,394,866 | 7/1983 | Hughes . |
| 4,402,329 | 9/1983 | Williams . |
| 4,444,195 | 4/1984 | Gold . |
| 4,497,326 | 2/1985 | Curry . |
| 4,567,901 | 2/1986 | Harris . |
| 4,602,645 | 7/1986 | Barrington et al. . |
| 4,624,265 | 11/1986 | Grassi . |
| 4,627,439 | 12/1986 | Harris . |
| 4,643,201 | 2/1987 | Stokes . |
| 4,664,120 | 5/1987 | Hess . |
| 4,711,027 | 12/1987 | Harris . |
| 5,111,811 | 5/1992 | Smits . |
| 5,190,052 | 3/1993 | Schroeppel . |

*Primary Examiner*—Jeffrey R. Jastrzab

[57] ABSTRACT

A single-pass atrio-ventricular (A-V) pacing lead includes an elongated main lead body having an atrial electrode at the distal end thereof, and includes a ventricular branch which departs from the main lead body just proximal to the tip of the atrial electrode. The ventricular branch has a ventricular electrode at its distal tip. The main lead body includes a preformed "J"-shaped portion which, following proper implantation, projects the atrial electrode against a wall of the atrial appendage. The ventricular branch includes a preformed bend which curves in the opposite direction of the J-shaped portion so as to maintain the ventricular branch generally away from the wall of the atrial appendage. The lead includes a single lumen which extends through both the main lead body and the ventricular branch, allowing the lead to be implanted using a single stylet. When the styler is fully inserted within the lumen, an extension portion of the atrial electrode, including the electrode tip, rests alongside the straightened ventricular branch so as to present a low cross-sectional profile, facilitating transvenous implantation.

24 Claims, 7 Drawing Sheets

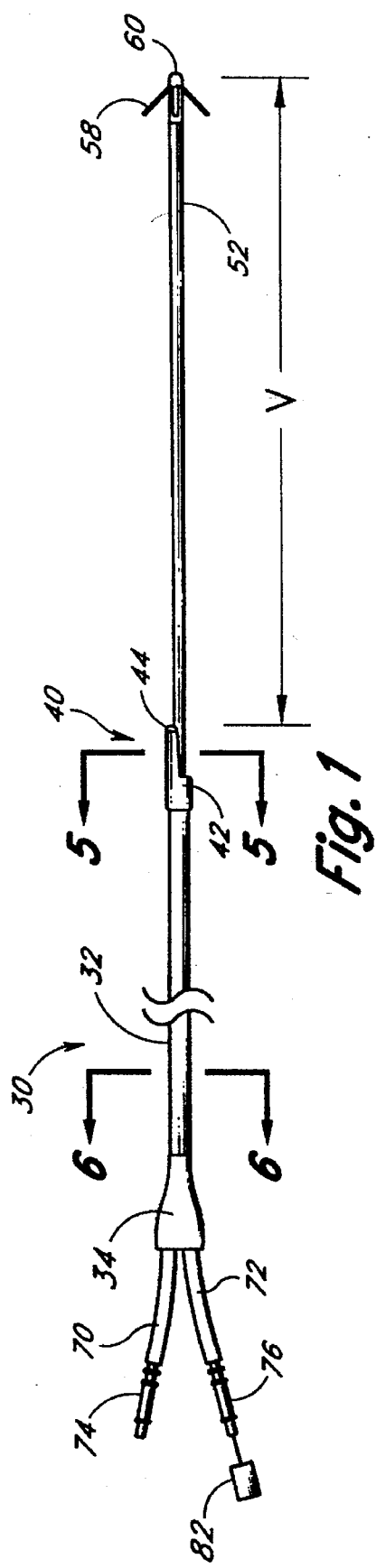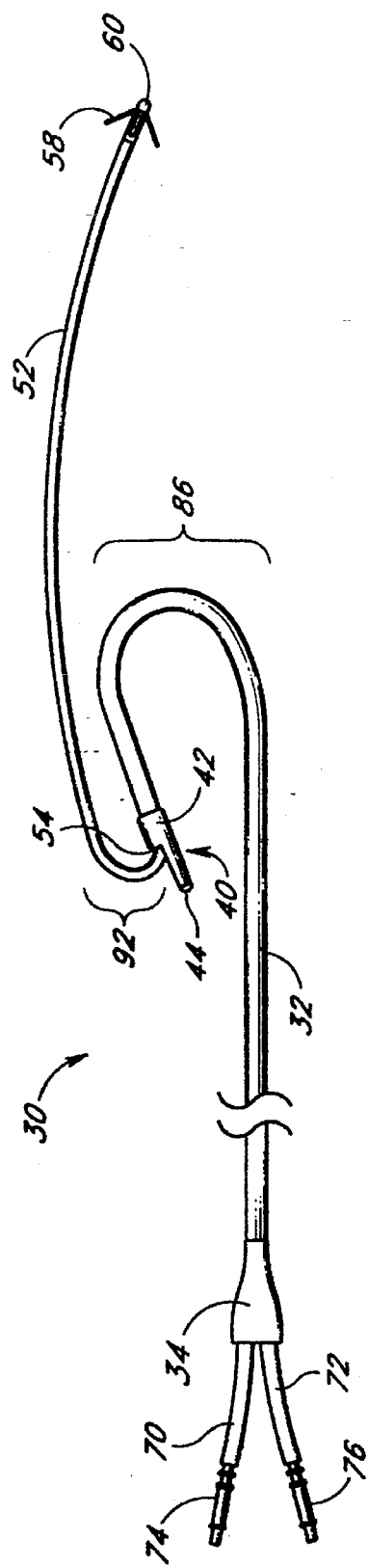

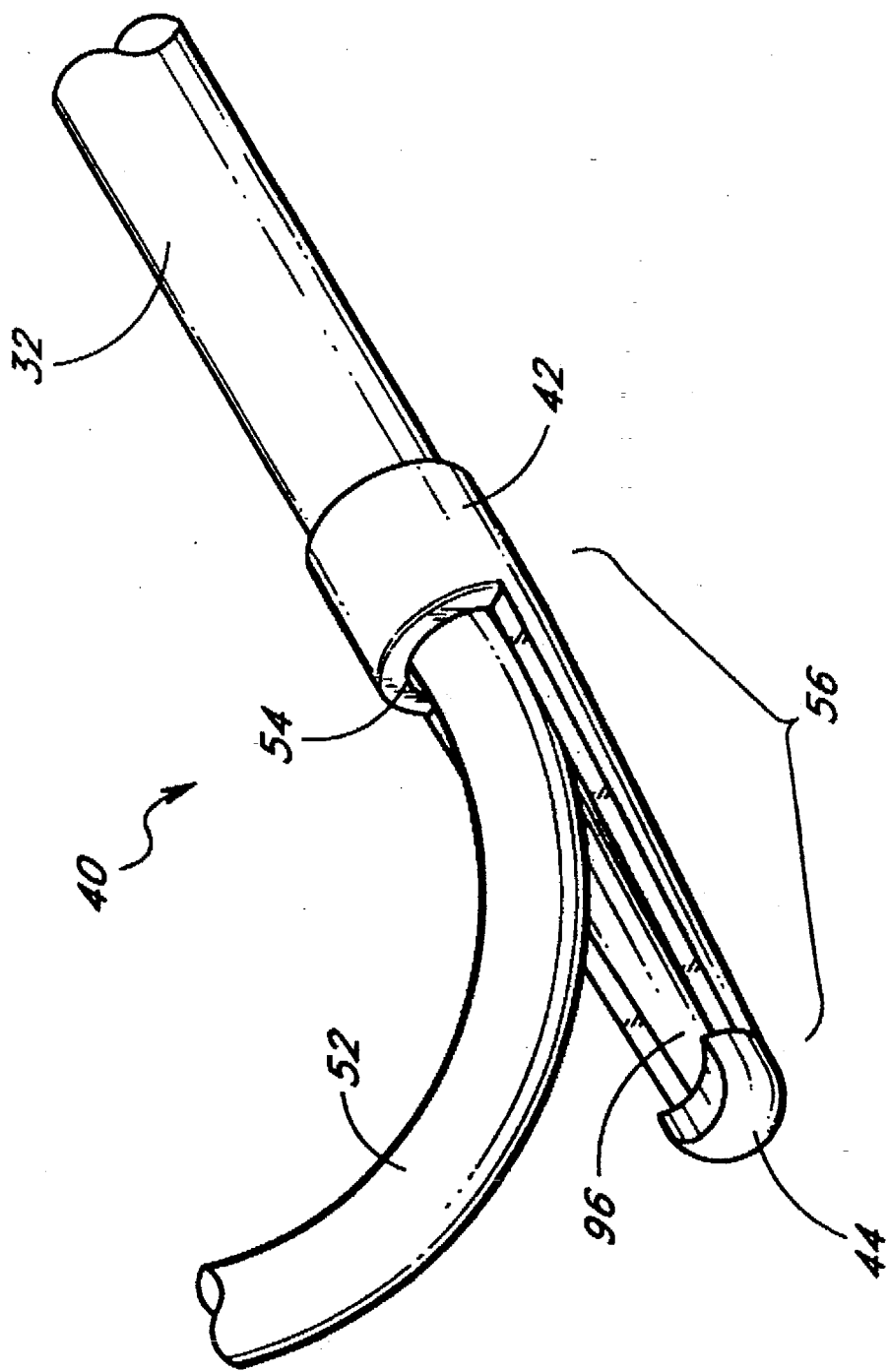

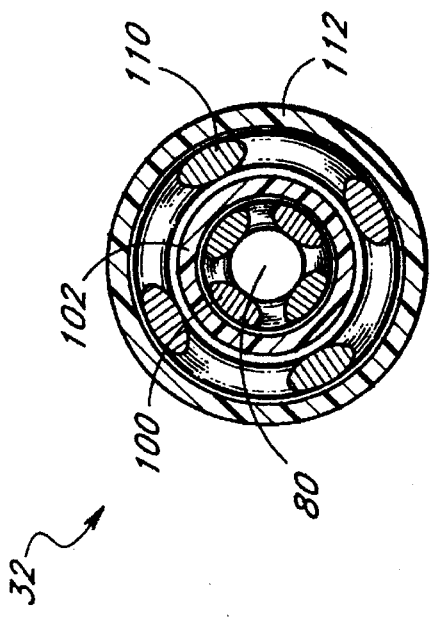
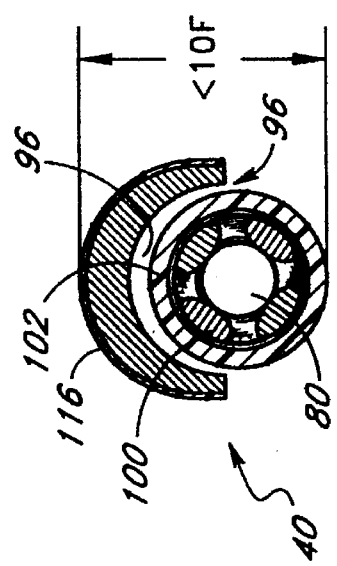
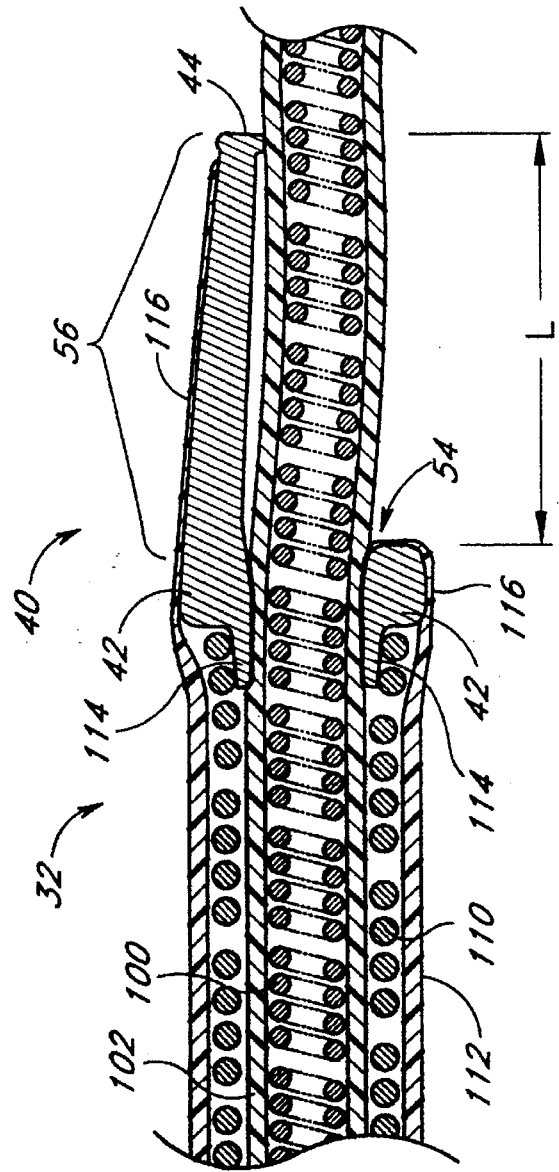

5,628,779

SINGLE-PASS A-V PACING LEAD

FIELD OF THE INVENTION

This invention relates to cardiac pacing leads, and more particularly, relates to single-pass atrioventricular (A-V) leads.

BACKGROUND OF THE INVENTION

Cardiac pacing involves the electrical stimulation of the heart in order to control the timing of the contractions of the heart. Electrical stimuli in the form of pulses are generated by an implantable, battery-powered pacemaker, and are applied to the tissue of the heart by one or more electrodes that are connected to the pacemaker via flexible, insulated conductors. The insulated conductors and associated electrodes form what is referred to as the "lead."

Implantation is typically performed by inserting the distal end of the lead into the patient's cephalic vein (one of the main veins from the upper arm), and forwarding the distal end through the subclavian vein and superior vena cava into the right side of the heart. To maintain the stiffness of the lead during implantation, a guidewire or "stylet" is typically inserted into a lumen (hollow channel) of the lead. Once the lead is properly positioned within the heart (using fluoroscopy to view the distal end of the lead), the stylet is withdrawn, and the proximal end of the lead is connected to the pacemaker. Finally, the pacemaker is implanted beneath the skin.

For various disorders it is desirable to pace the heart by applying separate electrical stimuli to the atrium and the ventricle of the right side of the heart. This form of pacing, commonly known as dual-chamber pacing, generally requires the placement of an atrial electrode in the right atrium and a ventricular electrode in the right ventricle. In addition to applying electrical stimuli to the tissue of the respective chambers, one or both of these electrodes may be used to sense intrinsic electrical activity, and to thereby detect timing abnormalities. For example, the pacemaker may sense the naturally-occurring electrical activity in the right atrium and use this information to generate appropriate electrical stimuli to apply to the right ventricle.

One problem with dual-chamber pacing has been the need to separately position and maintain the atrial and ventricular electrodes in contact with the electrically-sensitive tissue of the respective chambers. Under current practice, two separate leads are implanted within the patient's heart—an atrial lead which provides connectivity between the pacemaker and the tissue of the right atrium, and a ventricular lead which provides connectivity between the pacemaker and the tissue of the right ventricle. In addition, various styles of leads have been proposed which include both the atrial and ventricular electrodes on a single lead body. (See, for example, U.S. Pat. Nos. 4,154,247; 4,567,901; 4,643,201; 4,393,883; 4,497,326; and 4,711,027.) These leads are generally referred to as single-pass atrio-ventricular (A-V) leads. Although many different styles of single-pass A-V leads have been proposed, none of these leads have gained acceptance in the medical community.

Although the use of separate atrial and ventricular leads desirably permits the physician to independently manipulate and position the atrial and ventricular electrodes during implantation, the use of two leads also creates a number of potential problems. For example, the leads may become damaged as the result of abrasion as the leads rub against each other within a blood vessel and/or within the heart. Additionally, the use of two separate leads often increases the likelihood of "subclavian crush," which is the crushing of the lead hardware (typically during patient motion) between the first rib and the clavicle. Further, the use of two leads typically requires the physician to make a larger incision in the cephalic vein (or other blood vessel) than is necessary for the implantation of a single lead. These problems with the current practice can potentially be solved by the use of a suitable single-pass A-V lead.

In order to gain acceptance in the medical community, it is important that a single-pass A-V lead be easy to implant. Moreover, it would be desirable to provide a single-pass A-V lead for which the implantation procedure is highly similar to the procedure currently used by physicians for the implantation of separate atrial and ventricular leads; this would allow physicians to begin implanting the new lead with minimal training. The present invention seeks to provide a single-pass A-V lead having these and other advantageous characteristics.

SUMMARY OF THE INVENTION

The present invention provides a single-pass A-V pacing lead which is suitable for implantation using existing lead-positioning techniques that are well known by cardiologists. The lead may thus be implanted with minimal additional training.

In accordance with a preferred embodiment of the invention, the lead comprises a flexible, elongated main lead body having a distal end (which is positioned within the heart) and a proximal end (which connects to the implantable pacemaker). One or more pin connectors are provided at the proximal end to permit electrical and mechanical connection of the lead to an implantable pacemaker. An elongated atrial electrode is positioned at the distal tip of the main lead body for applying electrical stimuli (and/or sensing intrinsic electrical activity) within the right atrium. A distal portion of the main lead body is preformed (or "prebent") to assume a conventional atrial "J" configuration, so as to position the tip of the atrial electrode against a wall of the atrial appendage following proper implantation.

An elongated ventricular branch departs from the main lead body from just above (proximal to) the tip of the atrial electrode (preferably 4 to 16 millimeters from the tip), but below (distal to) the curved portion of the atrial "J." The ventricular branch includes a ventricular electrode at its distal tip for applying electrical stimuli (and/or sensing intrinsic electrical activity) within the right ventricle, preferably at the right ventricular apex just below the atrial electrode, the ventricular branch is preformed to curve in a direction generally opposite the direction of curvature of the atrial "J," so as to maintain the ventricular branch generally away from the wall of the atrial appendage. This helps to ensure that the atrial electrode will make good electrical contact with the tissue of the atrial appendage.

A single lumen extends through both the main lead body and the ventricular branch (beginning at the proximal end of the lead and terminating at the ventricular electrode), permitting the insertion of a relatively stiff stylet. When the stylet is fully inserted, both the preformed atrial J portion and the preformed portion of the ventricular branch are maintained in a generally straight configuration, as is desirable for transvenous implantation; this causes the distal portion of the atrial electrode (including the electrode tip) to rest alongside the straightened ventricular branch, presenting a low cross-sectional profile for implantation. To further reduce the cross-sectional profile during implantation, a groove or channel is preferably formed along the outer surface of the atrial electrode to receive an outer portion of the stiffened ventricular branch. As the stylet is withdrawn, the atrial electrode tip moves away from the ventricular branch (as the result of the preformed bend therein), and the atrial electrode tip is projected outward against the wall of the atrial appendage, without interference from the ventricular branch.

A preferred implantation procedure makes use of well known techniques for the implantation of standard ventricular and atrial J type leads. Initially, the lead is advanced transvenously with the stylet fully inserted, until the ventricular electrode is positioned in the right ventricular apex. The stylet is then partially withdrawn, and the lead is advanced distally to slacken the ventricular branch within the right ventricle. This technique is similar to the current practice for the implantation of standard ventricular leads.

As the stylet is withdrawn further, the tip of the atrial electrode departs from the ventricular branch, and the main lead body begins to assume its preformed atrial J configuration. The main lead body and the stylet are then manipulated by the physician to position the atrial electrode within the atrial appendage. This technique of positioning the atrial electrode is virtually identical to the current practice for the implantation of standard atrial J type leads. Finally, the stylet is fully withdraw, and the proximal end of the lead is connected to an implantable pacemaker.

Because the lead requires only a single stylet, the lead can be constructed with a low cross-sectional area, and can be implanted without the need to manipulate multiple stylets.

BRIEF DESCRIPTION OF THE DRAWINGS

These and other features of the invention will now be described with reference to the drawings of certain preferred embodiments, which are intended to illustrate and not to limit the invention, and in which:

FIG. 1 is a plan view of a single-pass A-V lead in accordance with a preferred embodiment of the present invention, illustrating the general configuration of the lead when a stylet is fully inserted within a lumen of the lead.

FIG. 2 is a plan view of the lead of FIG. 1, illustrating the general configuration assumed by the lead when the stylet is removed.

FIG. 4 is an enlarged perspective view of a portion of the lead of FIG. 1, illustrating a ventricular branch of the lead extending from an opening in the atrial electrode.

FIG. 5 is a cross-sectional view taken on the line 5—5 of FIG. 1.

FIG. 6 is a cross-sectional view taken along the line 6—6 of FIG. 2.

FIG. 7 is a longitudinal sectional view of the atrial electrode region of the lead.

DETAILED DESCRIPTION OF THE PREFERRED EMBODIMENTS

Figure 3:
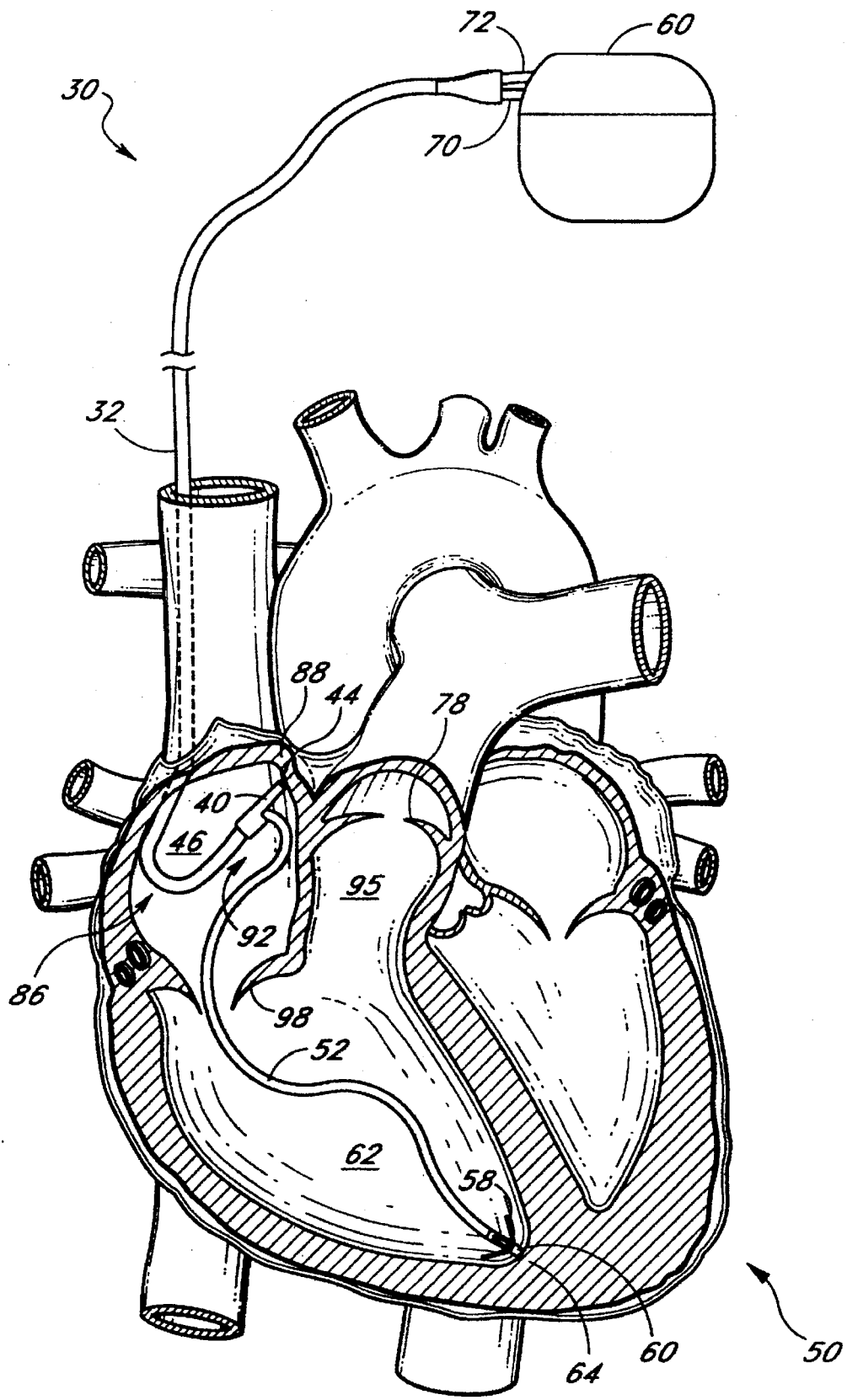
FIG. 3 is a perspective view in partial cross section, illustrating the lead of FIG. 1 implanted within a human heart.

FIGS. 1–7 illustrate a single-pass A-V lead 30 in accordance with a preferred embodiment of the present invention.

The lead 30 comprises a flexible main body 32 ("main body") which extends between a bifurcation boot 34 and an elongated atrial electrode 40. The atrial electrode 40 has a hollow base portion 42, and includes an electrode tip 44 for applying electrical stimuli to the tissue of the right atrium 46 (FIG. 3) of a human heart 50. A flexible ventricular branch 52 extends through the hollow base portion 42 of the atrial electrode 40 and then extends distally from an opening 54 in the base portion 42. The opening 54 is spaced proximally from the electrode tip 44 by a distance L (FIG. 7), which is seven millimeters in the preferred embodiment. The elongated portion 56 extending between the opening 54 and the electrode tip 44 will be referred to herein as the "extension portion." As discussed below, the departure of the ventricular branch 52 from the main body 32 just below the tip 44 of the atrial electrode 40 significantly facilitates lead implantation, while allowing the atrial electrode to maintain good contact with the tissue of the right atrium.

At the distal end of the ventricular branch 52 there is provided a conventional passive-fixation type ventricular electrode 60 for applying electrical stimuli to the tissue of the right ventricle 62 (FIG. 3), preferably at the right ventricular apex 64. The ventricular electrode 60 includes flexible tines 58 to accommodate the growth of fibrous tissue around the electrode 60. In other embodiments, an active fixation type electrode that uses a retractable barb or screw to hold the electrode 60 in position may be used. Additionally, although the illustrated atrial and ventricular electrodes 40, 60 are of the unipolar type, the lead may readily be adapted to use bipolar electrodes and/or could be actively fixated (e.g., with a helix electrode) as is known in the art.

The lead 30 also includes two flexible connector branches 70, 72 which extend proximally from the bifurcation boot 34 to allow the lead 30 to be connected to a pacemaker 60 (FIG. 3). Conventional IS-1 type pin connectors 74, 76 are provided at the proximal ends of the respective connector branches 70, 72. One of the pin connectors 74 is electrically connected to the atrial electrode 40, and the other pin connector 76 is electrically connected to the ventricular electrode 60. In other embodiments, the atrial and ventricular pin connectors 74, 76 may be replaced with a single, unified pin connector.

A hollow channel or "lumen" 80 (FIGS. 5 and 6) extends distally from the ventricular pin connector 76 substantially to the ventricular electrode 60, allowing a relatively stiff guidewire or "stylet" 82 (FIG. 1) to be inserted into the lead 30 during implantation. The stylet 82 is shown in FIG. 1 in a fully-inserted position, maintaining the lead body 32 and ventricular branch 52 in a substantially straight configuration (as is desirable for transvenous implantation).

With reference primarily to FIGS. 2 and 3, the main body 32 includes a preformed atrial "J" portion 86 which is configured to produce a "J"-shaped configuration when the stylet 82 is removed. The curvature, stiffness and configuration of this preformed atrial "J" portion 86 are preferably similar or identical to the curvature, stiffness and configuration of the prebent portion of a conventional atrial J type lead, such as the Model 1242 pacing lead available from Pacesetter, Inc. As with conventional atrial "J" leads, the preformed atrial "J" portion 86 of the present lead 30 is configured so as to bias the tip 44 of the atrial electrode 40 against a wall of the atrial appendage 88 (FIG. 3). The 2–3 centimeter segment of the main lead body 32 falling between the atrial electrode tip 44 and the preformed atrial "J" portion 86, including the atrial electrode 44, is generally straight in configuration.

With further reference to FIGS. 2 and 3, the ventricular branch 52 includes a preformed bend 92 which curves in the opposite direction (but generally within the same plane) as the preformed atrial "J" portion 86, toward the right ventricle 62. This preformed bend 92 begins at the atrial electrode 40, and extends distally for approximately five millimeters. With reference to FIG. 3, the curvature and stiffness of the preformed bend 92, coupled with the separation between the tip 44 and the opening 54 in the atrial electrode (discussed below), are sufficient to maintain the ventricular branch 52 generally away from the wall of the atrial appendage 88. This helps to ensure that the tip 44 of the atrial electrode 40 will make good contact with the tissue of the right atrium 46.

In the preferred embodiment, the portion of the ventricular branch 52 falling below (distal to) the preformed bend 92 is not preformed (i.e., has a generally straight configuration when in a relaxed state). In other embodiments, however, the ventricular branch 52 may include a second preformed bend which projects the ventricular electrode 60 upward into the right ventricular outflow (RVOT) 95. As described in copending U.S. application No. 08/629,959, filed concurrently herewith, entitled SINGLE-PASS A-V LEAD FOR PACING WITH STIMULATION OF RIGHT VENTRICULAR OUTFLOW TRACT, stimulation within the RVOT has been found to produce an improved sequence of activation.

With reference to FIGS. 4 and 6, the extension portion 56 of the atrial electrode 40 extends longitudinally, with a slight taper, from the opening 54 (from which the ventricular branch 52 extends) to the electrode tip 44. During implantation of the lead 30 with the stylet 82 fully inserted, this extension portion 56 lies flat against the ventricular branch 52 (as shown in FIGS. 1 and 8A), allowing the lead to move freely through the blood vessels. To provide a low cross-sectional profile during implantation, the extension portion 56 has a groove or channel 96 (FIGS. 4 and 5) formed longitudinally therealong to accept the straightened ventricular branch 52 during implantation. As illustrated in FIG. 5, the maximum width of this region of the lead is less than 10 French ("10F"), where 1 French=0.013 inches, when the stylet 82 is inserted.

One important advantage to having the ventricular branch 52 depart from the main body 32 just below the atrial electrode tip 44, as opposed to higher (proximally) along the main body 32, is that it allows the lead to be implanted using a single stylet 82. This is in contrast to leads that have separate atrial and ventricular branches, such as the leads disclosed in U.S. Pat. Nos. 4,567,901 to Harris and U.S. Pat. No. 4,643,201 to Stokes, for which two separate stylets are required. In addition to simplifying the implantation procedure over multi-stylet designs, the use of a single stylet generally allows the lead to be constructed with a smaller cross-sectional area. Another important advantage to having the branch 52 depart from the main body 32 close to electrode tip 44 is that it essentially eliminates the concern that the atrial and ventricular "branches" will separate and take different paths during insertion. Other features of the invention which contribute to the lead's ease of implantation are discussed below with reference to FIGS. 8 and 9.

As will be apparent from the foregoing, an important parameter of the present invention is the length L of the extension portion 56. If the extension portion 56 is too short, the preformed bend 92 of the ventricular branch 52 will contact the wall of the atrial appendage 88. On the other hand, if the extension portion 56 is too long, it becomes more difficult to maintain the rigid extension portion 56 and the flexible ventricular branch 52 side-by-side as the lead is inserted. (Unless these two lead portions 52, 56 are maintained directly along side one another during implantation, the lead 30 may become hung-up within a blood vessel.) Although the minimum length which can be used depends in large part on the curvature of the preformed bend 92 (with a tighter curve allowing for a smaller L), it has been found that a length L in the range of 4 to 16 millimeters is suitable.

FIG. 3 illustrates the lead 30 following proper implantation within a human heart 50. The preformed atrial "J" portion 86 of the lead serves to bias the atrial electrode 40 against an inner wall of the atrial appendage 88, as with conventional atrial J type pacing leads. The ventricular branch 52 extends downward through the tricuspid valve 98 and into the right ventricle 62, with the ventricular electrode 60 positioned at the ventricular apex 64. The pacemaker 60 provides electrical stimulation to the atrial appendage 88 and/or ventricular apex 64 in accordance with well known pacing techniques.

As generally illustrated in FIG. 3, the ventricular branch 52 is of sufficient length V (FIG. 1) to remain slack within the right ventricle 62 as the heart contracts. This helps to ensure that the electrodes 40, 60 will not be pulled out of position. Preferably, V is in the range of 12 to 22 centimeters.

The inner construction of the lead will now be described with reference to FIGS. 5–7. The main lead body 32 comprises an inner helical coil 100 and an outer helical coil 110. The coils 100, 110 are arranged in coaxial relationship to one another, and are separated by an inner insulating layer 102. In other embodiments, the coils 100, 110 may be arranged co-linearly (side-by-side), or may be replaced with straight-wire conductors. An outer insulating layer 112 surrounds and insulates the outer coil 110.

The inner coil 100 and surrounding insulating layer 102 form an inner lead body which extends from the ventricular electrode 60 to the ventricular pin connector 76 (FIGS. 1 and 2), with the inner coil 100 conductively connecting the ventricular pin connector 76 to the ventricular electrode 60. The inner walls of the coil 100 define the lumen 80 into which the stylet 82 (FIG. 1) may be inserted. As best seen in FIG. 7, this inner lead body extends though the hollow base portion 42 of the atrial electrode 40, and departs from the main body 32 at the opening 54. The inner lead body also extends through the bifurcation boot 34 (FIGS. 1 and 2).

The outer lead body, which is formed by the outer coil 110 and the outer insulating layer 112, extends from the atrial electrode 40 to the bifurcation boot 34, with the outer coil 110 continuing on to the atrial pin connector 74 to provide a conductive connection between the pin connector 74 and the atrial electrode 40. Within the bifurcation boot 34, the outer coil 110 unwinds temporarily (not shown) to allow the inner and outer coils 100 and 110 to depart from one another, as is conventional with coaxial leads; the outer coil 110 then re-forms (not shown), with a smaller diameter, within the insulating material of the connector branch 70. The inner and outer insulating layers 102, 112 are preferably in the form of a conventional silicone rubber tubing, into which the respective coils 100, 110 are inserted during manufacture. The inner and outer coils 100, 110 are preferably conventional quadfilar (4 wire) coils, as generally illustrated by FIGS. 6 and 7. (As is well known in the art, multifilar coils protect against wire breakage by providing multiple electrically-redundant wires wound in parallel.) The inner coil 100 is preferably formed from 0.004-inch diameter wire, and the outer coil 110 is preferably formed from 0.008-inch diameter wire. Because the inner coil 100 is formed from wire of a smaller diameter, the ventricular branch 52 is considerably more flexible (when the stylet 82 is removed) than the main body 32. With reference to FIG. 7, the distal end of the outer coil 110 slides over (and is laser-welded to) a flange 114 of the atrial electrode 40.

The preformed bend 92 (FIGS. 2 and 3) in the ventricular branch 52 is preferably formed within the insulating layer 102 only. This produces a relaxed curve which is sufficient to maintain the ventricular branch 52 away from the atrial wall in the region of the atrial electrode 40. The preformed bend 92 is formed using a conventional extruding and curing process in which the silicone tubing 102 is extruded, placed on a mandrel of appropriate curvature, heated, and then cured. In other embodiments, the preformed bend 92 may additionally or alternatively be formed in the inner coil 100.

The preformed atrial "J" portion 86 (FIGS. 2 and 3) in the main body 32 is preferably formed in both the outer coil 110 and the surrounding insulating layer (silicone tubing) 112. This provides for a relatively stiff curve which is sufficient to maintain the atrial electrode tip 44 in contact with a wall of 10 the atrial appendage 88 (FIG. 3). The preformed atrial "J" portion 86 is formed in the outer tubing 112 using the above-described extruding and curing process. The preformed atrial "J" portion 86 is similarly formed in the outer coil 110 by placing the coil over a mandril (of appropriate curvature) and then heating the coil, as is conventional in the art. The flexible nature of the helical coils 100, 110 and of the insulating layers 102, 112, permits the preformed atrial "J" portion 86 and the preformed bend 92 to be held in substantially straight configurations by the relatively stiff stylet 82.

With reference to FIGS. 5 and 7, the outer surface of the atrial electrode 40, with the exception of the electrode tip 44, is preferably coated with a thin insulating material 116 such as Parylene-C, available from Specialty Coating Systems, Inc., Ontario, Calif. The coating 116 reduces unnecessary discharge of electrical energy into the bloodstream, and thereby increases the battery life of the pacemaker.

A preferred method for implanting the lead 30 within a human heart 50 will now be described with reference to FIGS. 8 and 9, which illustrate intermediate stages during an implantation procedure. As will be apparent to those skilled in the art, this method advantageously makes use of the steps currently practiced by physicians in implanting separate atrial and ventricular pacing leads.

The region surrounding the atrial electrode 40 is preferably coated with a blood-soluble sugar derivative (not shown) such as mannitol, as generally described in U.S. Pat. No. 4,876,109 to Mayer et al, with the stylet 82 fully inserted. This coating encapsulates the area surrounding extension portion 56 of the atrial electrode 40 and preformed bend 92 in the ventricular branch 52. The mannitol encapsulation acts to maintain the extension portion 56 against the preformed bend 92 and thus reduces the likelihood that the extension portion 56 of the atrial electrode 40 will become hung-up as the lead is advanced intravenously. The coating will typically be applied during the manufacture of the lead.

Figure 8:
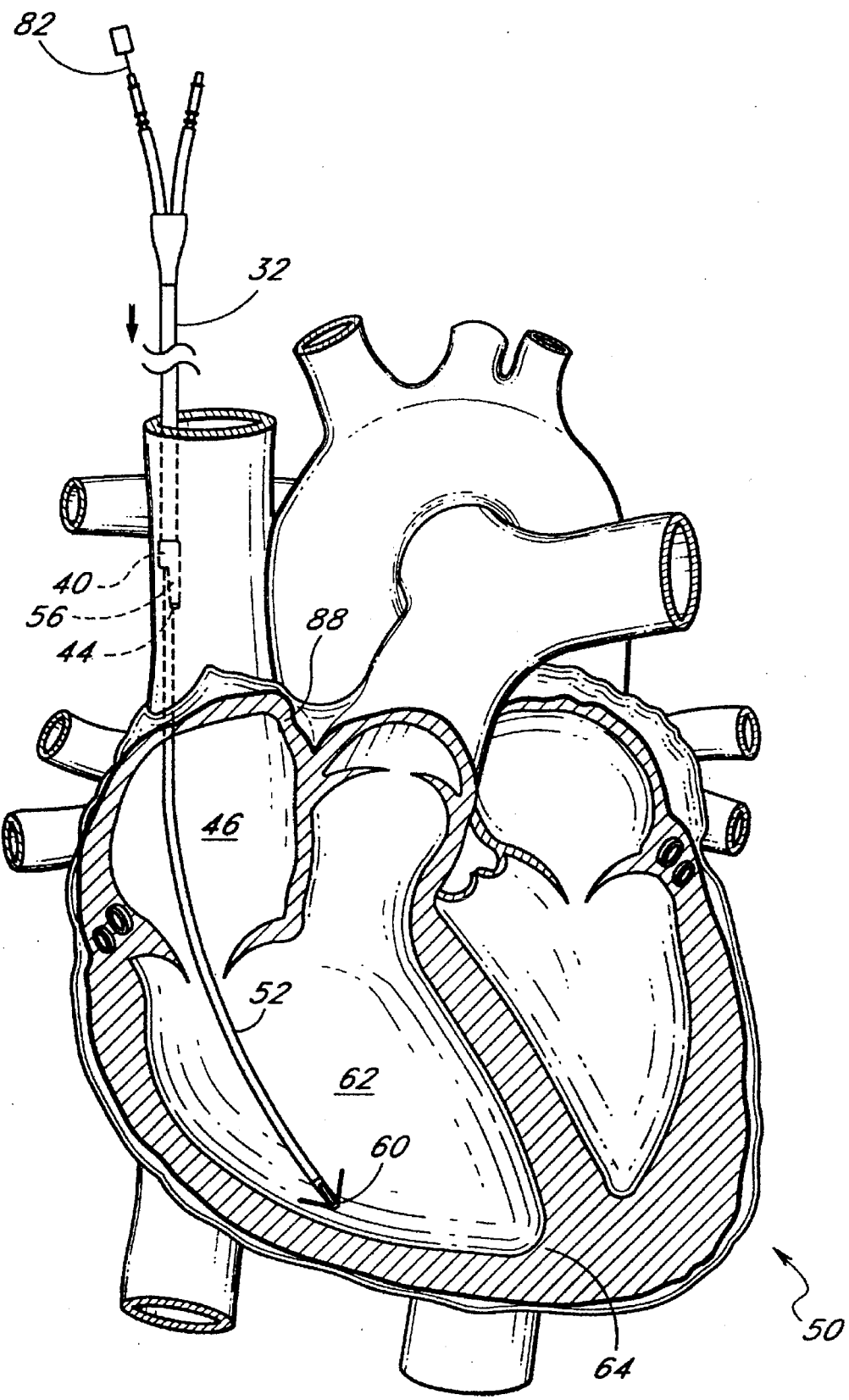
FIGS. 8 and 9 illustrate intermediate stages during the implantation of the lead.

With reference to FIG. 8, the lead 30 is initially introduced transvenously (using a conventional introducer) with the stylet 82 fully inserted, and is advanced until the ventricular electrode 60 reaches the right ventricular apex 64. As illustrated in FIG. 8, the extension portion 56, including the atrial electrode tip 44, rests alongside the stiffened ventricular branch 52 as the lead 30 is advanced distally. With reference to FIG. 9, once the ventricular electrode 60 is properly positioned within the apex 64, the physician partially withdraws the stylet 82, and then advances the lead 30 distally several centimeters to cause the ventricular branch 52 to become slack within the right ventricle 62. This general procedure of advancing the lead, positioning the ventricular electrode 60 in the apex 64, and then creating a slack region by partially withdrawing the stylet 82 and further advancing the lead, is virtually identical to the current practice for implanting ventricular pacing leads.

Figure 9:
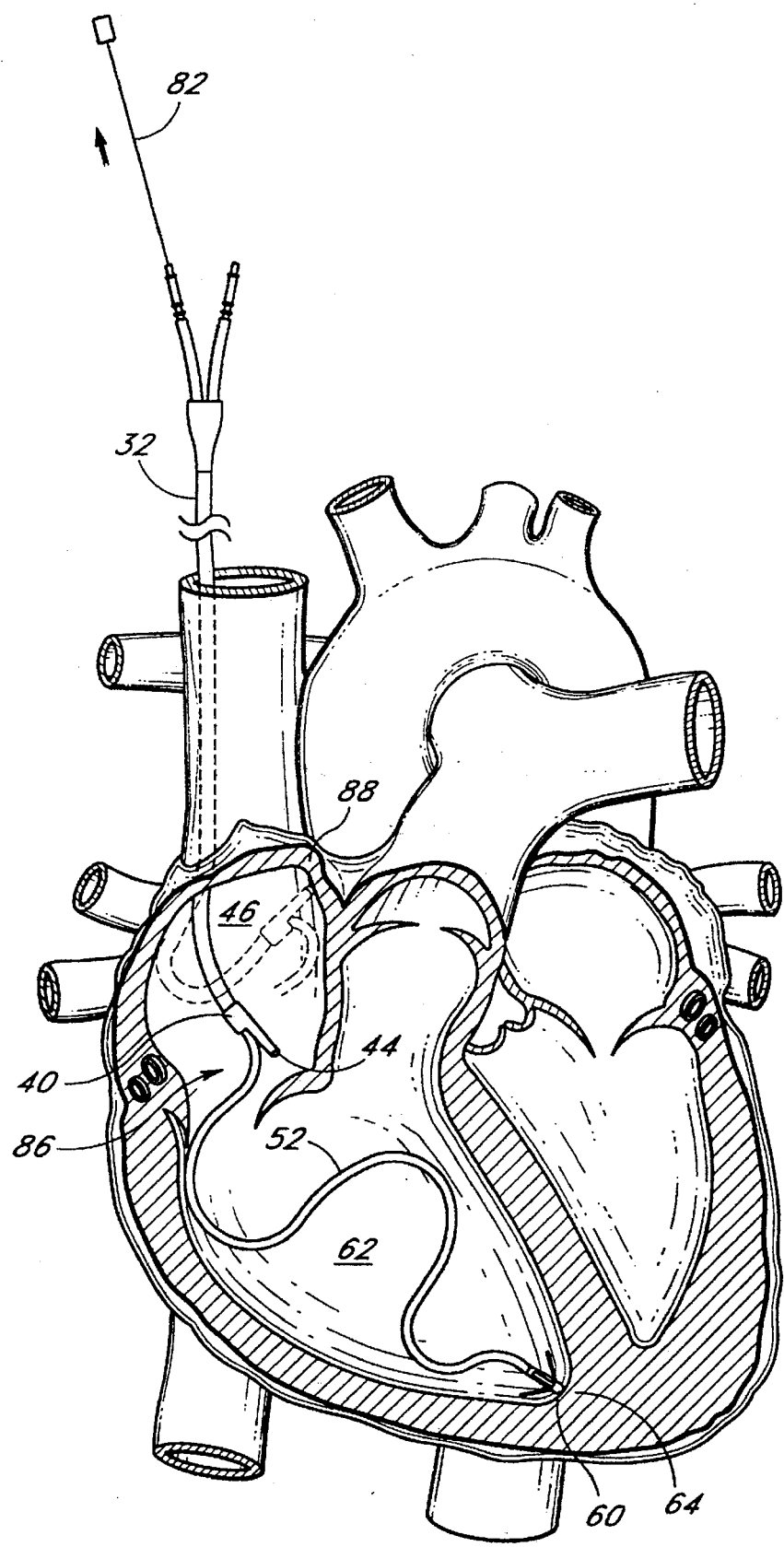

The remainder of the procedure, which is illustrated generally by FIG. 9 (and FIG. 3, which illustrates the final position of the lead), is highly similar to the current practice for implanting standard atrial J pacing leads. With the stylet 82 inserted to about the atrial electrode 40, the physician positions the straightened atrial "J" portion 86 of the lead within the right atrium 46, and then begins to withdraw the stylet 82 to allow the atrial "J" to form (as shown in phantom in FIG. 8B). (As illustrated in FIG. 8B, the ventricular branch 52 separates from the atrial electrode tip 44 when the stylet 82 is withdrawn from the atrial "J" portion 86 of the ventricular branch.) During this process of withdrawing the stylet, the physician may advance, withdrawn and/or rotate the lead 30 as necessary to allow the "J" to properly form. Once the atrial electrode 40 is properly positioned within the atrial appendage 88, the stylet 82 is fully withdrawn, and the atrial and ventricular pin connectors 74, 76 are inserted into the respective receptacles (not shown) of the pacemaker's connector block.

As will be apparent from the foregoing, the lead 30 may advantageously be implanted using techniques that are well known to cardiologists, with little or no special training.

Figure 10:
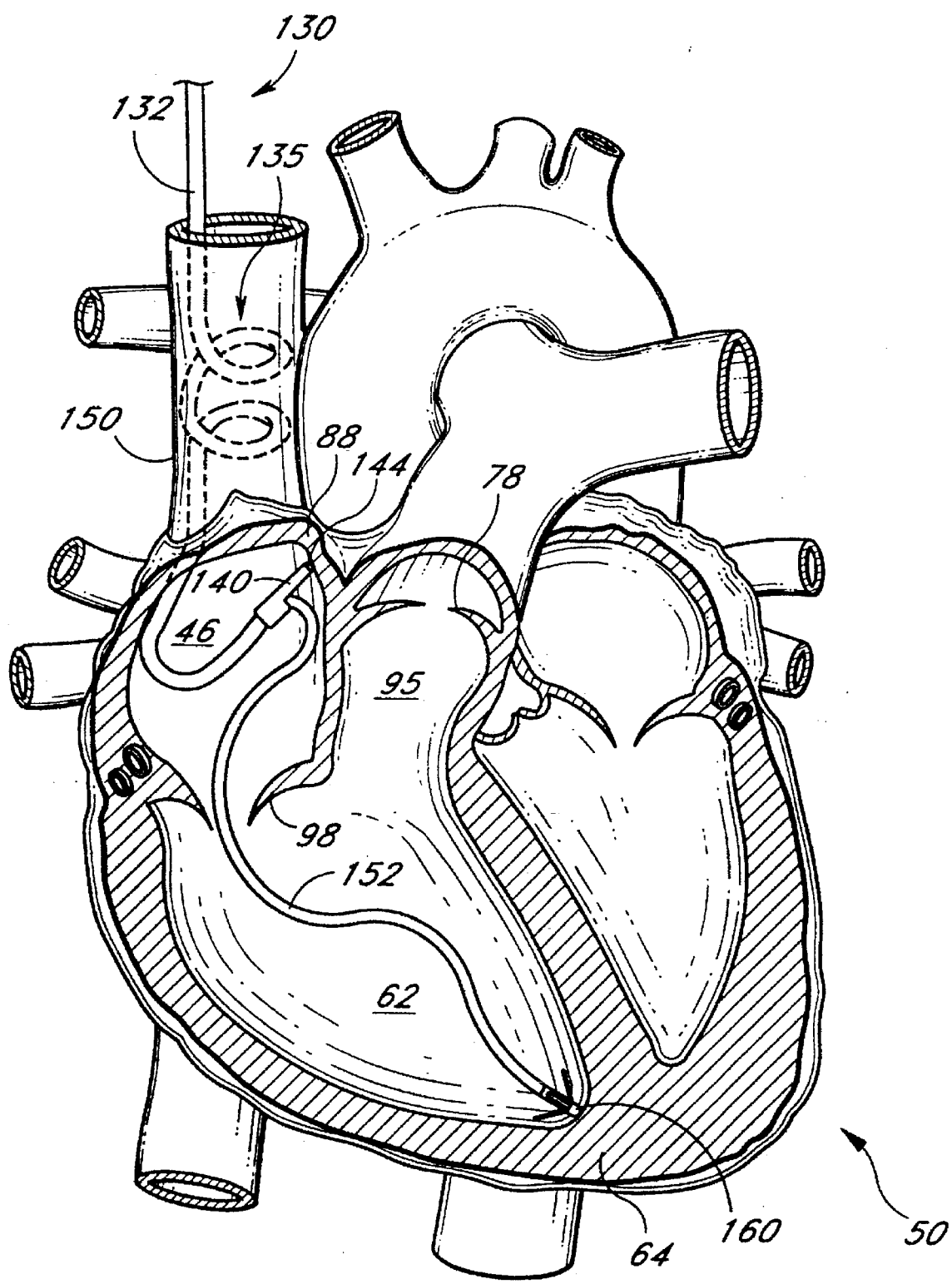
FIG. 10 is a perspective view illustrating a lead in accordance with another embodiment of the present invention.

FIG. 10 illustrates a single-pass A-V lead 130 in accordance with an alternative embodiment of the invention, with the lead shown following proper implantation. Like reference numbers preceded with the digit "1" are used in FIG. 10 to illustrate elements that appear in the preceding drawings. The lead 130 is identical in all respects to the lead 30 of FIGS. 1–8, with the exception that the lead includes a preformed helix 135 in the-main body 132, several centimeters proximal to the atrial J portion 186. The helix 135 is of sufficient diameter to contact and push outward against the inner walls of the superior vena cava 150, and to thereby provide additional lead stability. The helix 135 is preferably formed within the outer coil 110 (FIGS. 6 and 7) of the main body 132 using the coil shaping techniques described above.

While certain preferred embodiments of a single-pass A-V lead have been described, these embodiments have been presented by way of example only, and are not intended to limit the scope of the present invention. Thus, the breadth and scope of the present invention should be defined only in accordance with the following claims and their equivalents.

What is claimed is:

1. A single-pass A-V pacing lead, comprising:

an elongated main lead body having a proximal end and a distal end, and having an atrial electrode at a distal tip thereof and a conductor attached to the atrial electrode and extending to the proximal end of the main lead body, the main lead body including a preformed J-shaped portion at the distal end, the J-shaped portion configured so as to bias a tip of the atrial electrode against a wall of the atrial appendage of a human heart when the lead is properly implanted; and an elongated ventricular branch having a ventricular electrode at a distal tip thereof and a conductor attached to the ventricular electrode and extending to the proximal end of the main lead body, the ventricular branch departing from the main lead body proximal to the tip of the atrial electrode but distal to a curve of the J-shaped portion, at least a portion of the ventricular branch being prebent to maintain the ventricular branch away from the wall of the atrial appendage.

2. The single-pass A-V pacing lead as in claim 1, wherein a single lumen extends longitudinally within the main lead body and the ventricular branch, allowing both the J-shaped portion of the main lead body and the prebent portion of the ventricular branch to be straightened for implantation using a single stylet.

3. The single-pass A-V pacing lead as in claim 2, wherein the atrial electrode includes an extension portion which projects the atrial electrode tip generally away from the ventricular branch when the lead is implanted, and wherein the extension portion and the atrial electrode tip rest alongside the ventricular branch when the stylet is fully inserted.

4. The single-pass A-V pacing lead as in claim 3, wherein a channel is formed longitudinally along the extension portion, the channel configured to receive an outer portion of the ventricular branch when the stylet is inserted.

5. The single-pass A-V pacing lead as in claim 1, wherein the ventricular branch departs from the main lead body 4 to 16 millimeters from the atrial electrode tip.

6. The single-pass A-V pacing lead as in claim 1, wherein the ventricular branch departs from the main lead body along a substantially straight portion of the main lead body, the substantially straight portion extending from the atrial electrode tip to the curve.

7. The single-pass A-V pacing lead as in claim 1, wherein the ventricular branch departs from the main lead body through an opening in a side portion of the main lead body, the opening spaced proximally from the electrode tip by 4 to 16 millimeters.

8. The single-pass A-V pacing lead as in claim 7, wherein the opening is formed in a base portion of the atrial electrode.

9. The single-pass A-V pacing lead as in claim 1, wherein the J-shaped portion has substantially the same configuration and stiffness as a J-shaped portion of a conventional atrial J type pacing lead.

10. The single-pass A-V pacing lead as in claim 1, wherein the ventricular branch is configured to position the ventricular electrode within the right ventricular apex of a human heart.

11. The single-pass A-V pacing lead as in claim 1, wherein the main lead body additionally includes a preformed helix-shaped portion proximal to the J-shaped portion, the helix-shaped portion configured to press outward against the inner walls of the superior vena cava when the lead is properly implanted, the helix-shaped portion thereby holding the lead in position following implantation.

12. A single-pass A-V pacing lead, comprising:
an elongated main lead body having an atrial electrode at a distal end thereof and a conductor attached to the atrial electrode and extending to the proximal end of the main lead body, an atrial portion of the lead body being preformed to assume a curved configuration when the lead body is in a relaxed state, the preformed atrial portion being configured so as to bias the atrial electrode against a wall of the right atrium of a human heart;
an elongated ventricular branch which branches from the main lead body proximal to a distal tip of the atrial electrode, the ventricular branch having a ventricular electrode at a distal end thereof and a conductor attached to the ventricular electrode and extending to the proximal end of the main lead body for applying electrical stimuli to the right ventricle of the heart, at least a portion of the ventricular branch being preformed to assume a curved configuration; and
a lumen which extends longitudinally within the main lead body and the ventricular branch to permit the insertion and withdrawal of a stylet, the lumen extending through the preformed portions of the main lead body and the ventricular branch and sized to receive a single stylet through both of the preformed portions, whereby the lead may be implanted using the single stylet.

13. The single-pass A-V pacing lead as in claim 12, wherein the preformed portion of the ventricular branch and the preformed atrial portion curve in generally opposite directions.

14. The single-pass A-V pacing lead as in claim 12, wherein the preformed portion of the main lead body is configured to position the atrial electrode against a wall of the atrial appendage.

15. The single-pass A-V pacing lead as in claim 12, wherein the ventricular branch branches from the main lead body distal to the preformed atrial portion.

16. The single-pass A-V pacing lead as in claim 12, wherein the ventricular branch branches from the main lead body from 4 to 16 millimeters from the distal tip of the atrial electrode.

17. The single-pass A-V pacing lead as in claim 12, wherein the preformed portion of the ventricular branch is configured to maintain the ventricular branch generally away from the wall of the right atrium, to thereby ensure good electrical contact between the atrial electrode and the wall of the right atrium.

18. The single-pass A-V pacing lead as in claim 12, wherein the atrial electrode includes an extension portion which projects the tip generally away from the ventricular branch when the lead is properly positioned within the heart, and wherein the extension portion rests alongside the ventricular branch when the stylet is fully inserted within the lumen.

19. The single-pass A-V pacing lead as in claim 18, wherein the extension portion includes a longitudinal indentation, the indentation configured to receive an outer surface of the ventricular branch when the stylet is inserted, the indentation thereby reducing a cross-sectional area of the lead during implantation.

20. The single-pass A-V pacing lead as in claim 12, wherein the ventricular branch is configured to position the ventricular electrode within the right ventricular apex of the heart.

21. The single-pass A-V pacing lead as in claim 12, wherein the main lead body additionally includes a preformed helix portion which assumes a helix configuration when the stylet is withdrawn from the lumen, the helix portion configured to press outward against the inner walls of the superior vena cava when the lead is properly implanted within the heart.

22. A method of pacing a human heart, comprising the steps of:
providing a single-pass A-V pacing lead having a main lead body and having a ventricular branch which extends distally from the main lead body, the lead having a lumen which extends longitudinally within the main lead body and the ventricular branch;
advancing the lead transvenously with a single stylet fully inserted within the lumen to position a ventricular electrode within the right ventricular apex of the heart, the ventricular electrode located at a distal end of the ventricular branch;

partially withdrawing the stylet from the lumen to allow the ventricular branch to assume a relaxed configuration, and to allow a preformed portion of the main lead body to begin to assume a final J-shaped configuration within the right atrium;

manipulating the lead and the stylet to position an atrial electrode within the atrial appendage of the heart, the atrial electrode located at a distal end of the main lead body;

fully withdrawing the stylet from the lumen; and applying electrical stimuli to the atrial appendage and/or the ventricular apex of the heart via the lead.

23. The method of pacing a human heart as in claim 22, wherein the step of manipulating the main lead body comprises advancing the lead distally to slacken the ventricular branch within the right ventricle.

24. The method of pacing a human heart as in claim 22, wherein the step of partially withdrawing the stylet from the lumen allows a preformed portion of the ventricular branch to assume a preformed curved configuration, the curved configuration being sufficient to maintain the ventricular branch generally away from the wall of the atrial appendage following implantation.

* * * * *